United States Patent
Terada et al.

(10) Patent No.: US 7,544,935 B2
(45) Date of Patent: Jun. 9, 2009

(54) METHOD AND APPARATUS FOR EVALUATING THIN FILMS

(75) Inventors: Shohei Terada, Hitachi (JP); Kazutoshi Kaji, Hitachi (JP); Tatsumi Hirano, Hitachinaka (JP); Gyeong-su Park, Gyeonggi-do (KR); Se-ahn Song, Seoul (KR); Jong-bong Park, Gyeonggi-do (KR)

(73) Assignees: Hitachi, Ltd., Tokyo (JP); Hitachi High-Technologies Corporation, Tokyo (JP); Samsung Electronics Co., Suwon (KR)

( * ) Notice: Subject to any disclaimer, the term of this patent is extended or adjusted under 35 U.S.C. 154(b) by 179 days.

(21) Appl. No.: 11/296,641

(22) Filed: Dec. 8, 2005

(65) Prior Publication Data
US 2006/0145075 A1 Jul. 6, 2006

(30) Foreign Application Priority Data
Dec. 8, 2004 (JP) ............................. 2004-354949

(51) Int. Cl.
*G01N 23/04* (2006.01)
(52) U.S. Cl. ..................... 250/306; 250/307; 250/310; 250/311
(58) Field of Classification Search ................. 250/306, 250/307, 310, 311
See application file for complete search history.

(56) References Cited

U.S. PATENT DOCUMENTS

2004/0188608 A1* 9/2004 Kaneyama .................. 250/305
2004/0211899 A1* 10/2004 Ezumi et al. ................ 250/310

FOREIGN PATENT DOCUMENTS

JP 07-311165 11/1995

OTHER PUBLICATIONS

Grogger, et al. "Energy-filtering TEM at high magnification: spatial resolution and detection limits" Ultramicroscopy 96 (2003) 481-489.*

* cited by examiner

*Primary Examiner*—David A. Vanore
*Assistant Examiner*—Michael Maskell
(74) *Attorney, Agent, or Firm*—Antonelli, Terry, Stout & Kraus, LLP.

(57) ABSTRACT

A method for evaluating thin films comprises the steps of inputting measurement conditions, generating electron beams from an electron source to condense the electron beams to a specimen by a condenser lens, enlarging the electron beams transmitted by the specimen with imaging lenses to image an enlarged image of the specimen, acquiring elemental maps of the specimen with an element analyzer to display the acquired elemental maps, measuring a length of the elemental maps, and correcting the measurement conditions. Disclosed is an evaluating apparatus that implements the above evaluating method.

18 Claims, 8 Drawing Sheets

TRANSMISSION ELECTRON MICROSCOPE IMAGE

INTENSITY PROFILE FROM WHITE LINE PORITON

ELEMENTAL MAP OF Cr

INTENSITY PROFILE FROM WHITE LINE PORITON

FIG. 8A
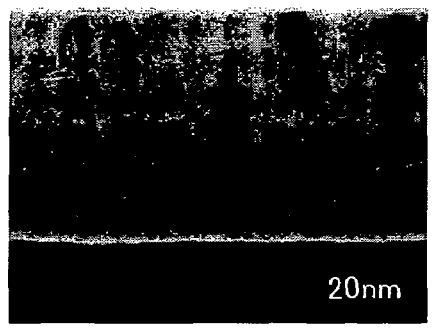
FIG. 8B
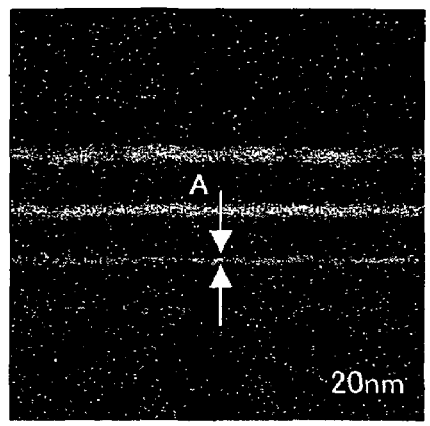
FIG. 8C
| MEASUREMENT LOCATION | MEASUREMENT RESULT (BEFORE CORRECTION) | MEASUREMENT RESULT (AFTER CORRECTION) |
|---|---|---|
| A | 1.4 nm | 1.1 nm |

METHOD AND APPARATUS FOR EVALUATING THIN FILMS

CLAIM OF PRIORITY

This application claims priority from Japanese application serial No. 2004-354949, filed on Dec. 8, 2004, the content of which is hereby incorporated by reference into this application.

FIELD OF THE INVENTION

The present invention relates to a method and an apparatus for evaluating thin films, which measure a length by using a photographic image obtained from an analyzer equipped to a transmission electron microscope or a scanning transmission electron microscope.

BACKGROUND OF THE INVENTION

Now, devices in which thin films are intentionally formed on a substrate for various purposes are manufactured on an industrial basis. Also, the thin films on the substrate, which are accidentally formed, may change the characteristics of the devices or material. For example, as semiconductor devices or magnetic head devices are miniaturized, the processing sizes (film thickness) that influence the device performance and a required precision in the film quality are extremely demanded more and more. When the semiconductor device is miniaturized as described above, and the design rule is set to 90 nm or lower, the gate oxide film of a semiconductor transistor is extremely thinned to about 1 nm. The film thickness greatly depends on physical characteristics such as a leak current or a dielectric constant within the transistor. Also, in the device structure of the magnetic head device, a magnetoresistance effect due to the spin dependent scattering of electrons that pass through a nonmagnetic layer or a barrier layer is utilized in any head structure of the nm structure. The head sensitivity largely depends on the film thickness. For that reason, a technique by which the film thickness of sub nm is evaluated with a high precision is one of important issues in developing the next generation of heads or mass-producing the heads with a stable sensitivity.

Up to now, an x-ray reflectometry instrument has been employed in the device for measuring the length of the thin films, as disclosed in Japanese Patent Laid-Open No. H7 (1995)-311165. In the case of the x-ray reflectometry instrument, a specimen resulting from laminating thin films in multi-layers is irradiated with x-rays to measure the x-ray reflectivity, the obtained patterns are analyzed, and an attempt is made to absolutely evaluate information on the thickness and reflectivity of the thin films and the density. Furthermore, this method using x-rays is advantageous in that the method can be conducted in the atmosphere, the method can be applied to an optically opaque system such as metal, and a nondestructive evaluation can be conducted.

Also, as a thin film evaluating method within a micro-area, there is conducted a direct observation using the transmission electron microscope. The thicknesses of films are measured from the photographic image by means of the transmission electron microscope as follows: First, a position of the specimen in an optically axial direction and a current value of an objective lens are fixed, the specimen having known dimensions is observed at a given magnification under predetermined conditions. Then, the excitation current of plural imaging lenses is adjusted in such a manner that a photographic image on an image display substantially coincides with the display magnification. The excitation conditions of the imaging lenses at that time are stored in association with the display magnification.

The same operation is conducted on other setting display magnifications, and the excitation conditions of the imaging lens corresponding to the respective display magnifications are recorded and saved, respectively. Setting the magnification is conducted by a moiré pattern or a crystal lattice image which is capable of determining the intervals through the electron diffraction method.

In the case of measuring an arbitrary film thickness within the photographic image, after the excitation conditions of the imaging lenses which are stored with respect to a certain magnification are reproduced, the photographic image is displayed on the image display, the sizes within the display image are measured, and an actual thickness is displayed according to the measurement magnification.

As described above, in the case of using x-rays in measurement of the thickness of the thin. film, the x-rays with which the specimen is irradiated cannot be focused more than about several micrometers. Therefore, measurement can be conducted when the film structure has the same lamination over the wide area, but the thickness of the thin film cannot be measured in the case where the film structure is identical in only the nanometers area.

The reason that an object can be observed with a transmission electron microscope image is because there is contrast in the electron intensity within the photographic image. Because the specimen which is observed by the transmission electron microscope is very thin in the transmission direction of electron beams, most of incident electrons are allowed to penetrate the interior of the specimen. In this case, the transmission electron microscope image uniformly brightly appears. However, the reason that an object can be observed with the transmission electron microscope image is because electrons are scattered within the specimen transmits the electrons. The intensity at which the electrons are scattered is attributed to the atomic scattering factor of the respective atoms within the specimen. For that reason, in the case where the atomic numbers of the elements that constitute the adjacent objects or films are close to each other in the visual field of observation, the atomic scattering factors are also values very close to each other, as a result of which there is little contrast of the transmission electron microscope image.

In recent years, there are analyzing manners such as an electron energy loss spectroscopy (EELS) in which the specimen is irradiated with electron beams, and loss transmission electrons are sorted into energies due to the mutual interaction between the incident electrons and the atoms within the specimen, and an energy dispersive x-ray spectroscopy (EDS or EDX) in which the characteristic x-ray that is generated from the specimen is analyzed by a semiconductor detector, in the transmission electron microscope or scanning transmission electron microscope each having an analyzer. Through those manners, the elemental maps that select the specific elements within the micro portion of the specimen are acquired, and an attempt is made to measure the arbitrary distances from the image. Since those analyzing manners are very high in spatial resolution to the degree of from several nanometers to several tens nanometers, and also selects only the elements to be observed, the contrast within the obtained image is sharp. However, there arises a problem on the imprecision of the length measurement function depending on the measurement conditions or the selected elements.

Under the above circumstances, the present invention has been made to solve the problems with the above-mentioned conventional film thickness measuring method and the evaluating apparatus. Therefore an object of the present invention is to measure the thickness of an ultra thin film with a high precision. Another object of the present invention is to a method and apparatus which are capable of measuring the film thickness in the thin film structure having no micro area or crystal structure.

SUMMARY OF THE INVENTION

In the present invention, a length measuring function in a photographic image that is obtained by an image pickup device is corrected according to device parameters or measurement conditions which are inherent to an electron microscope, and observed elements, and the image is displayed on an image display on the basis of the correction result.

That is, according to the present invention, there is provided a method for evaluating thin films, comprising the steps of: inputting measurement conditions; generating electron beams from an electron source to condense the electron beams to a specimen by a condenser lens; enlarging the electron beams transmitted by the specimen by imaging lenses to image an enlarged image of the specimen; acquiring elemental maps of the specimen by an element analyzer to display the acquired elemental maps; measuring a length of the elemental maps; and correcting the measurement conditions. In the above method, it is preferable that the elemental maps are acquired by one of an electron energy loss spectroscopy, an energy dispersive X-ray spectroscopy, and a cathode luminescence. Also, it is preferable to display a measurement mark that indicates a given length and a numeric value indicative of a length of the measurement mark on the elemental maps. Further, the measurement mark can be arbitrarily set in length and tilt.

Also, according to the present invention, there is provided an apparatus for evaluating thin films, comprising: an electron source that generates electron beams; a condenser lens that condenses the electron beams generated from the electron source to the specimen; a plurality of imaging lenses including an objective lens that enlarges electron beams transmitted by the specimen and images an enlarged image of the specimen; an analyzer that can acquire elemental maps; an image display that displays the elemental maps taken by the analyzer; a measurement condition input device that inputs the measurement condition; length measuring means for measuring the elemental maps in length; and a length measurement correcting device that corrects the length measuring means according to the measurement condition.

The apparatus for evaluating thin films can display a measurement mark that indicates a given length on the image display. The measurement mark that is displayed on the image display can arbitrarily set the display position or tilt. Also, the apparatus can display the length of the measurement mark displayed and the numeric value corresponding to the length. As a result, the length of a portion to be arbitrarily measured can be simply known.

In the case of displaying the transmission electron microscope image that has been taken by the image pickup device on the image display, an enlargement magnification at the time of photographing can be displayed on the image display. Also, in the case of measuring the length by the transmission electron microscope image, it is possible to measure the length by using the measurement function which is calculated by the respective magnifications in the image display.

As described above, according to the thin film evaluating apparatus of the present invention, the thickness of the ultra thin film can be measured with a high precision.

BRIEF DESCRIPTION OF THE DRAWINGS

FIGS. 8A to 8C are diagrams showing an example of length measurement in an elemental map of chrome by a thin film evaluating apparatus according to an embodiment of the present invention.

DETAILED DESCRIPTION OF THE PREFERRED EMBODIMENTS

Figure 1:
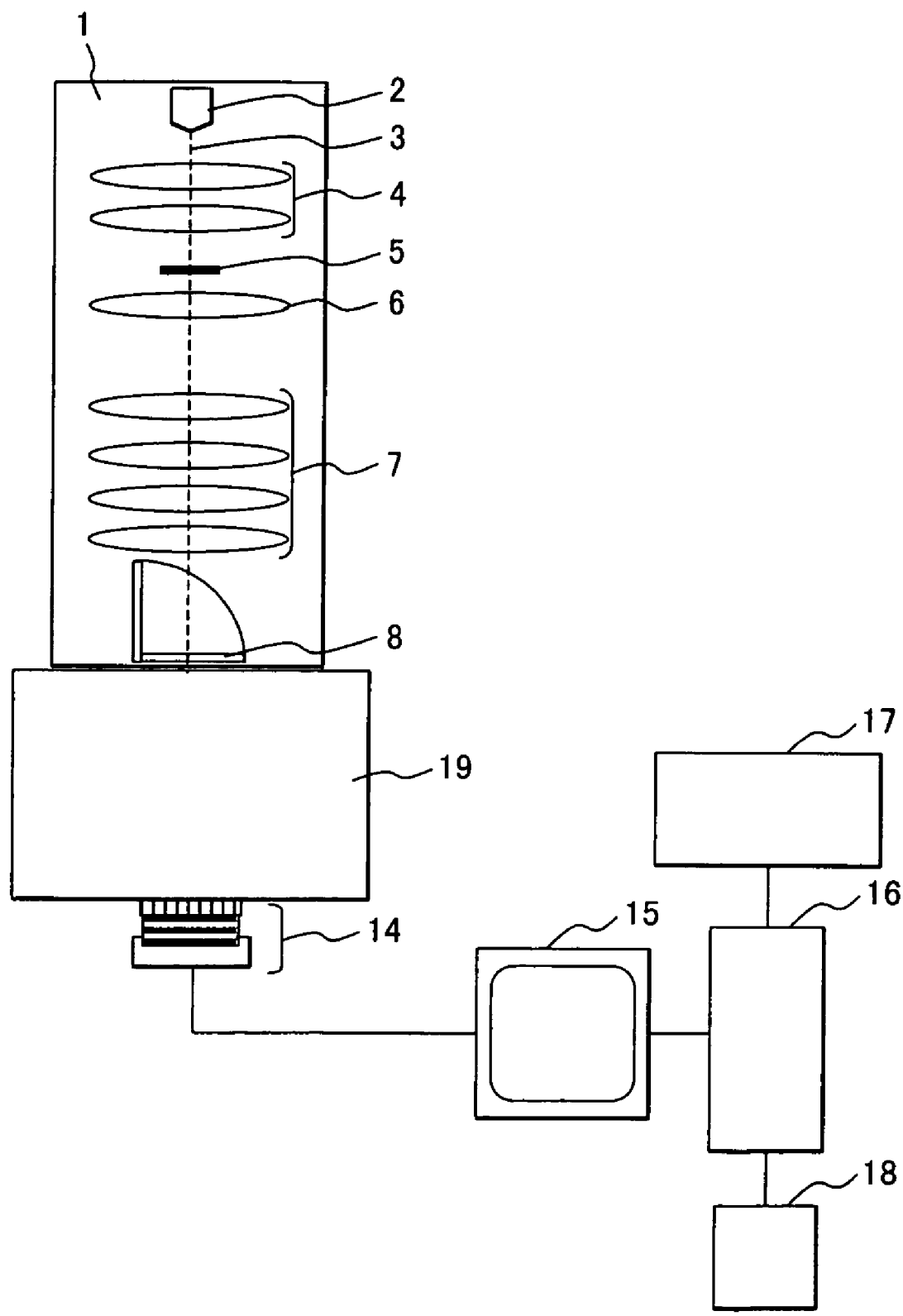
FIG. 1 is a schematic structural diagram showing an example of a transmission electron microscope with an electron spectroscopy according to the present invention.

Now, a description will be given of embodiments of the present invention with reference to the accompanying drawings. FIG. 1 is a diagram showing a schematic structure of a thin film evaluating apparatus according to the present invention, and a schematic view showing an example of a transmission electron microscope 1 and an electron spectroscopy 19 with which the transmission electron microscope 1 is equipped. An electron beam 3 emitted from an electron source 2 is accelerated and passes through a condenser lens system 4. A specimen 5 is irradiated with the passed electron beam 3. The electron beam 3 transmitted by the specimen 5 passes through an objective lens 6, and passes through plural imaging lenses 7.

The electron beam 3 that has passed through the transmission electron microscope 1 enters an electron spectroscopy 19 and is then imaged by an image pickup device 14, and thereafter displayed on an image display 15. A device condition value inherent to the transmission electron microscope and an observation condition value for obtaining an elemental map are inputted to a measurement condition input device 17.

A correction value (displacement amount) is calculated by a measurement correcting device 16 on the basis of the condition values that have been inputted to the measurement condition input device 17. An arbitrary location is selected from an image that is displayed on the image display 15, and the length is measured by using length measuring means 18. The length measured value is calculated according to the magnification of the transmission electron microscope. After calculation, an accurate measurement value is obtained according to a correction value (displacement amount) that has been obtained by the measurement correcting device 16.

When it is assumed that a chromatic aberration coefficient of the transmission electron microscope is $C_c$, an accelerating voltage of the electron beam is $E_o$, an energy select slit width is $\Delta E$, a divergence angle of the electron beam is $\beta$, a wavelength of the electron beam is $\lambda$, a spherical aberration coefficient is $C_s$, and a coefficient inherent to the elements that obtains the elemental map is $Z_z$, the measurement correcting device for correcting the elemental map obtained by the electron spectroscopy can correct the length measurement function by using the fact that the length measurement error $\Delta R$ is represented by the following relational expression.

$$\Delta R = \sqrt{d_c^2 + d_d^2 + d_s^2 + (Z_z)^2} \quad \text{(Ex 1)}$$

$$d_c = C_c \times \frac{\Delta E}{E_0} \times \beta$$

$$d_d = 0.61 \times \frac{\lambda}{\beta}$$

$$d_s = 0.5 \times C_s \times \beta^3$$

In the case where the elemental map is acquired by the transmission electron microscope with the electron spectroscopy, and the length is measured by using the image, an error in the length measurement occurs. This is because the error depends on the conditions of the device used in acquiring the elemental map, the conditions at the time of acquiring the elemental map, and the elements to be acquired. In general, the chromatic aberration coefficient of the transmission electron microscope is $C_c$, the accelerating voltage of the electron beam is $E_o$, the energy select slit width is $\Delta E$, a divergence angle of the electron beam is $\beta$, a wavelength of the electron beam is $\lambda$, a spherical aberration coefficient is $C_s$, and a coefficient inherent to the elements that obtains the elemental map is $Z_z$, the measurement error $\Delta R$ is obtained by the above expression (1). Therefore, when it is assumed that the length measurement obtained by the magnification of the transmission electron microscope is $R_T$, and the length measured value after correction is R, the length measured value R is represented by the following Expression 2.

$$R = \sqrt{R_T^2 - (\Delta R)^2} \quad \text{(Ex2)}$$

After the device conditions and the conditions at the time of acquiring the elemental map have been inputted to the measurement condition input device 17, the correction value is calculated by the measurement correcting device 16. Also, after an arbitrary location on an image that is displayed within the image display 15 is measured by the length measuring means 18, the measurement is corrected by the above-mentioned correcting method and the length measured value is displayed on the image display 15. The correction system is not limited to this example. After the elemental map has been acquired by means of an analyzer 19 with which the transmission electron microscope 1 is equipped, and the measurement displacement amount is calculated by the measurement correcting device 16 on the basis of the measurement condition that has been inputted to the measurement condition input device 17, and thereafter the measurement result at the arbitrary location is displayed on the image display device 15.

Figure 2:
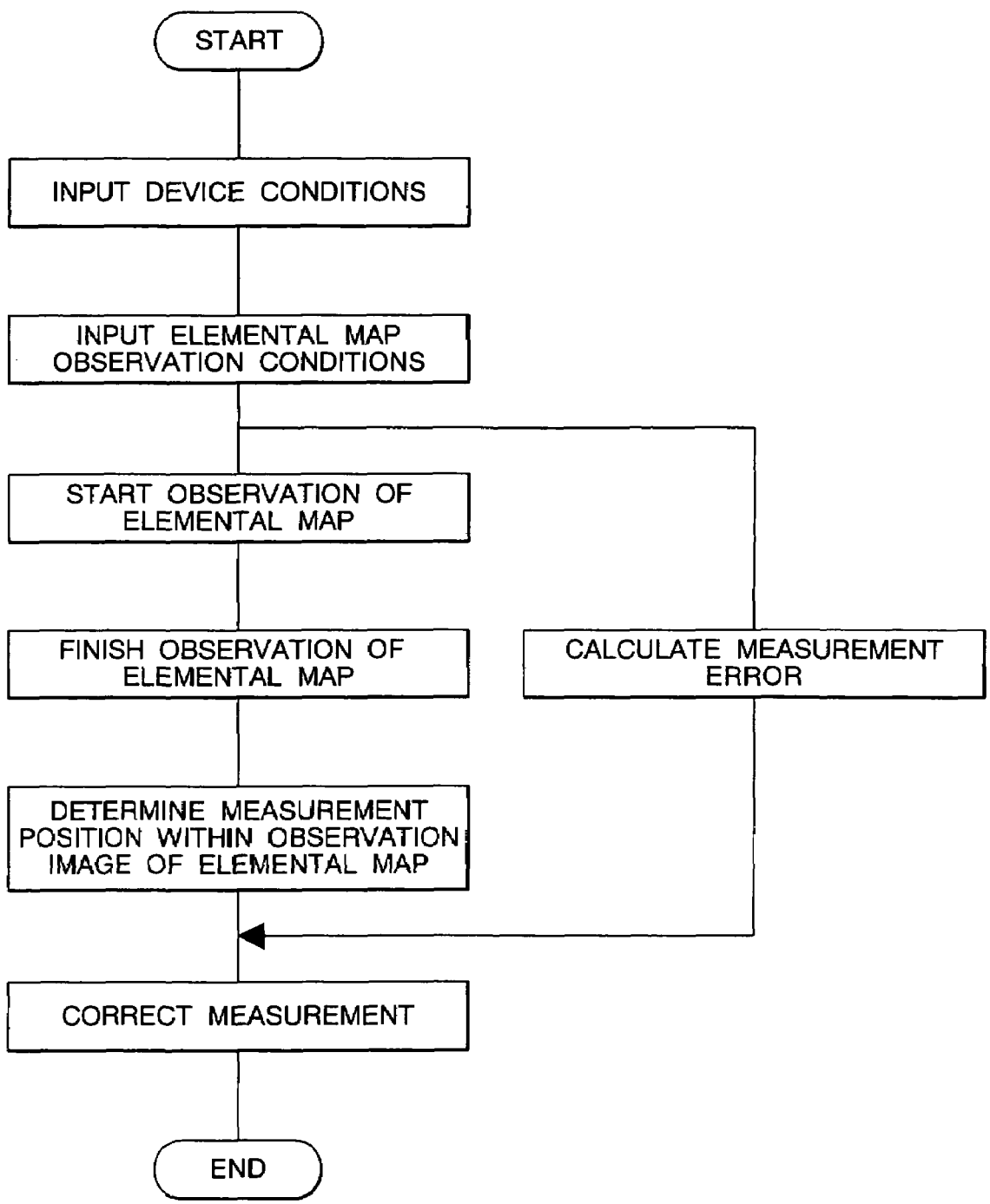
FIG. 2 is a flowchart showing a correction procedure of length measuring means with an elemental map according to the present invention.

FIG. 2 is a flowchart showing a procedure for correcting the length measuring means. First, the spherical aberration coefficient $C_s$ inherent to the transmission electron microscope and the chromatic aberration coefficient $C_c$ are inputted as the inputs of the device conditions. Since the input values are not changed so far as observation is made by using the same device, it is unnecessary to change the input values once those conditions are inputted.

Then, the observation conditions of the elemental map are inputted. In the case where the elemental map is observed by using the transmission electron microscope with the electron spectroscopy, the accelerating voltage $E_o$ of the electron beam, the divergence angle $\beta$ of the electron beam, the energy select slit width $\Delta E$, and the element Z that wants to acquire the elemental map are inputted. The wavelength $\lambda$ of the electron beam corresponding to the accelerating voltage $E_o$ is automatically calculated. After the condition value has been inputted, the observation of the elemental map starts. The corrected value (displacement amount) of the length measurement under the observation conditions is calculated at the same time as the observation. After the observation of the elemental map has been completed, a portion to be measured in length is designated within the elemental map. The portion and direction to be measured in the length can be arbitrarily conducted. The measurement value is corrected to an accurate length measurement value from the measurement value calculated on the basis of the magnification of the transmission electron microscope and the calculated measurement error $\Delta R$, and the processing is completed.

Figure 3A:
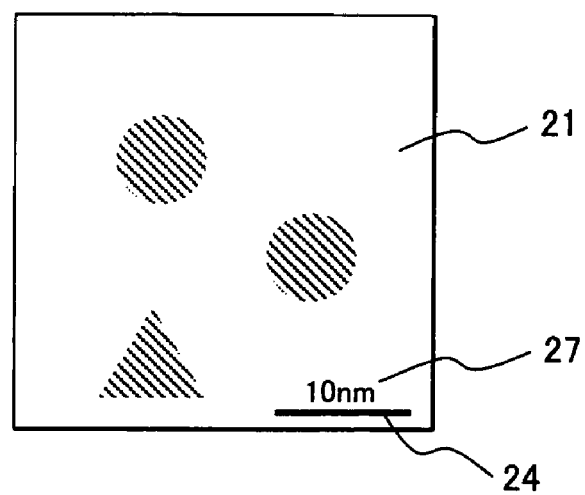
FIGS. 3A to 3C are diagrams for explaining the correction method of the measurement mark, respectively.
Figure 3B:
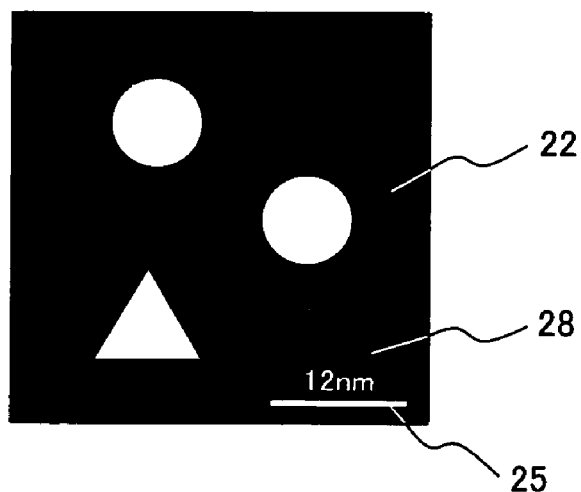
Figure 3C:
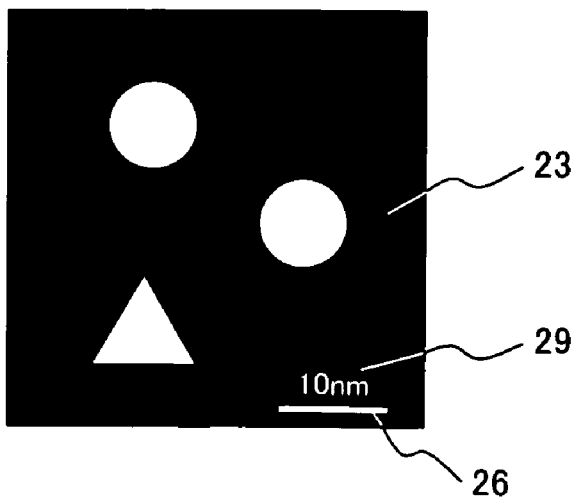

Also, the image display 15 can display the picked-up elemental map as well as the measurement mark and a numeric value representative of the length of a line segment of the measurement mark. FIGS. 3A to 3C are diagrams for explaining a method of correcting the measurement mark. FIG. 3A shows an example of the measurement mark indicated within a transmission electron microscope image 21. In FIG. 3A, the measurement mark 24 and a numeric value 27 indicative of the line segment of the measurement mark are displayed in the image. The numeric value 27 indicative of the line segment of the measurement mark is calculated on the basis of the magnification that is saved in the transmission electron microscope and displayed.

Subsequently, a description will be given of the display of the measurement mark and the numeric value indicative of the line segment of the measurement mark in the elemental map. Elemental maps 22 and 23 are shown in FIGS. 3B and 3C. It is assumed that when the measurement error is calculated in the elemental map as described above, the measured value is larger than the calculated value of the transmission electron microscope by about 20%. In this situation, a numeric value 28 indicative of the length of the line segment of the measurement mark is made larger than a numeric value 27 indicative of the line segment of the measurement mark displayed within the transmission electron microscope image 21 by about 20%, without changing the length of the measurement mark 25 which is displayed within the elemental map 22 as shown in FIG. 3B. Alternatively, as shown in FIG. 3C, a numeric value 26 indicative of the line segment of the measurement mark displays the same numeric value as a numeric value 24 displayed within the transmission electron microscope image 21, and the length of the measurement mark 26 may be corrected and displayed.

Figure 4:
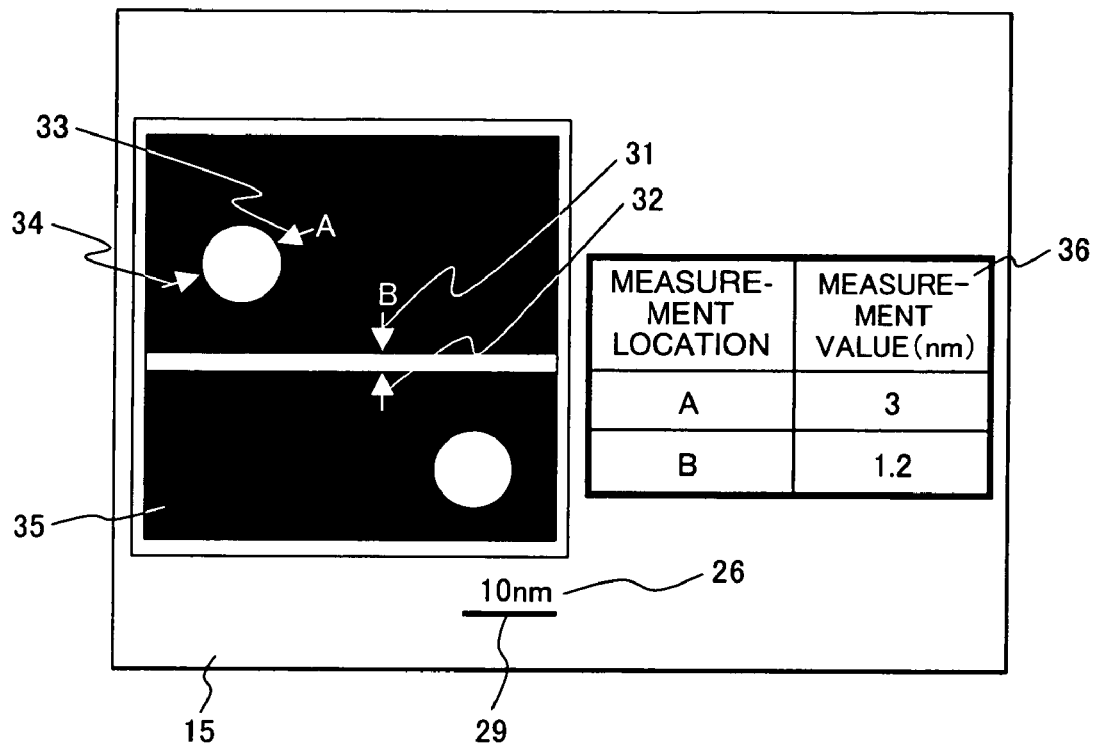
FIG. 4 is an explanatory diagram showing a case in which a length between measurement position designation marks is measured from an elemental distribution image.

FIG. 4 is an explanatory diagram in the case where a length between the measurement position designated marks is measured from the elemental map. Portions to be measured in length are designated by measurement position designation marks 31, 32, 33, and 34 from the elemental map 35 displayed in the image display 15. The measurement position designation marks can designate an arbitrary location, an arbitrary tilt, and an arbitrary length. The designated portions are two in this embodiment, but the present invention is not limited to this embodiment. Also, the measurement mark 26 after correcting the measurement error and the numeric value 29 indicative of the length of the line segment of the measurement mark are displayed in the image display 15. Further, after the measurement errors of the measurement values corresponding to the respective measurement locations are corrected, the corrected values are displayed in a measurement result display 36. The display method and the display contents in the present invention are not limited to this embodiment.

Figure 5:
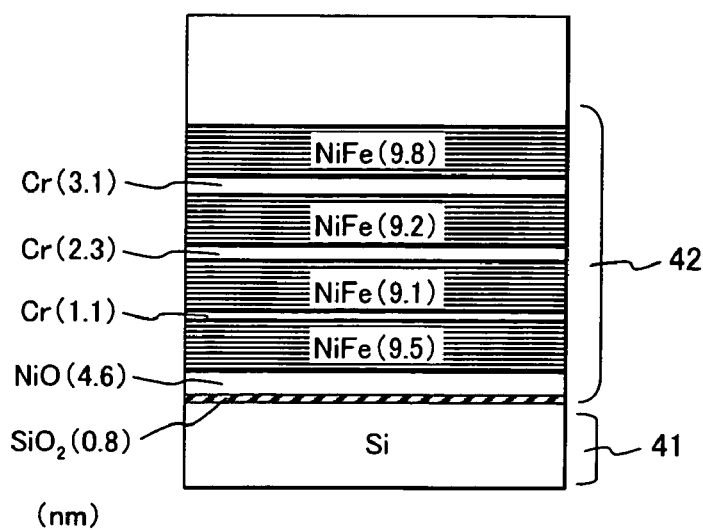
FIG. 5 is a schematic diagram for explaining a multi-layer film used in an embodiment.

Subsequently, a specific example of the above embodiment will be described. A schematic view of a specimen used in the observation is shown in FIG. 5. A specimen that multi-layer films 42 are laminated on a substrate 41 is observed. The substrate 41 is made of silicon, and the multi-layer films 42 on the substrate 41 are formed by depositing natural $SiO_2$ and NiO (5 nm) on the substrate 41 in the stated order, and thereafter depositing NiFe (10 nm), Cr (1 nm), NiFe (10 nm), Cr (2 nm), NiFe (10 nm), Cr (3 nm), and NiFe (10 nm) thereon in the stated order. Numeric values enclosed within parentheses are design values.

Before the elemental map is observed by the transmission electron microscope and the electron spectroscopy, an experiment is made to check how much the design film thickness coincides with the actual film thickness. The result is shown in the parentheses of FIG. 5. In the case of this embodiment, because the area of the laminated films are several micrometers, and are not configured such as the device structure of a semiconductor, measurement can be made by the x-ray reflectivity. Then, the laminated specimen is cut off, and ion-milled after having been mechanically polished so that the final thickness of the specimen in the transmission direction of the electron beam is set to 0.05 μm.

The observation through the transmission electron microscope is conducted under the conditions where an accelerating voltage is 197 kV, a divergence angle of the electron beam is 4.4 mrad, and the observation magnification is 200,000 times power. The observation energy position in the electron spectroscopy is set to 574 eV of Cr, and the width of an energy select slit is set to 30 eV. Also, the spherical aberration coefficient ($C_s$) of an objective lens in the transmission electron microscope is 1.2 mm, and the chromatic aberration coefficient ($C_c$) is 1.5 mm. An image pickup device 14 for recording an image is a CCD camera of 1024×1024 pixels. The draft amount of the specimen is suppressed to a small value of 0.005 nm/sec.

Figure 6A:
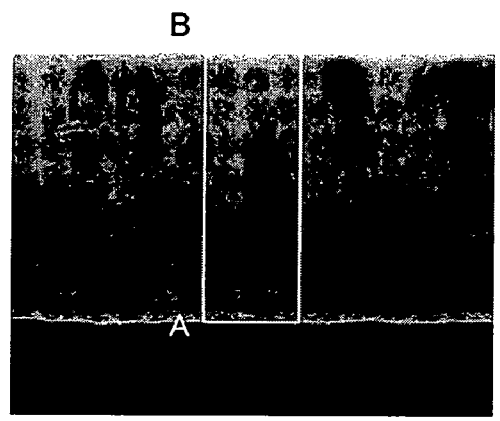
FIG. 6A is a diagram showing a transmission electron microscope image in a thin film evaluating apparatus according to an embodiment of the present invention.
Figure 6B:
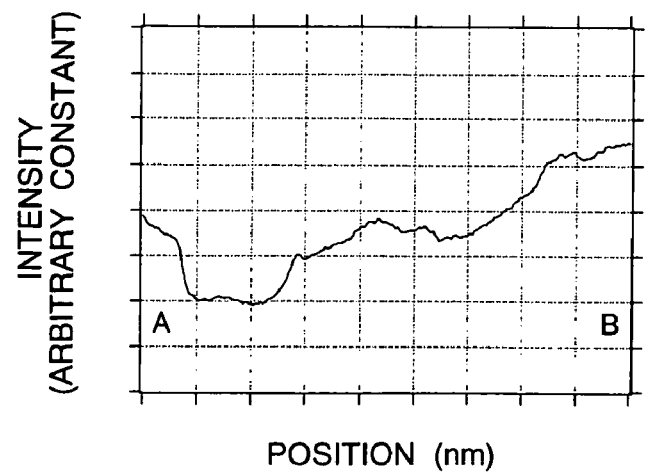
FIG. 6B is a graph showing an intensity profile of the transmission electron microscope image.

FIG. 6A shows the normal transmission electron microscope image taken under the above conditions. Also, FIG. 6B shows an intensity profile that is obtained from a white line portion shown in the transmission electron microscope in FIG. 6A. It is difficult to discriminate a chrome layer and a ferronickel layer from the intensity profile. This is because there is little difference in atomic confusion factor, and the contrast is low in the transmission electron microscope image since the atomic number of Cr, the atomic number of Ni, and the atomic number of Fe are very close to each other.

Figure 7A:
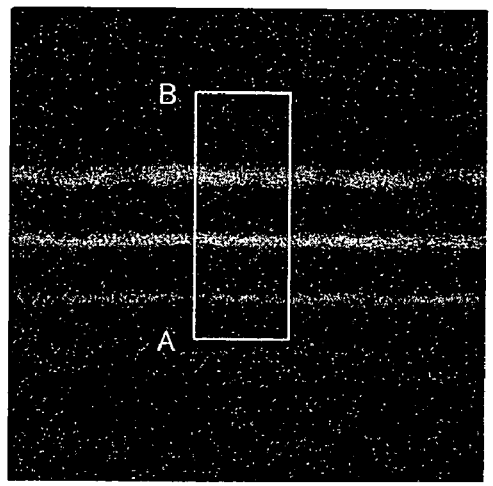
FIG. 7A is a diagram showing an elemental map of chrome obtained by in a thin film evaluating apparatus according to an embodiment of the present invention.
Figure 7B:
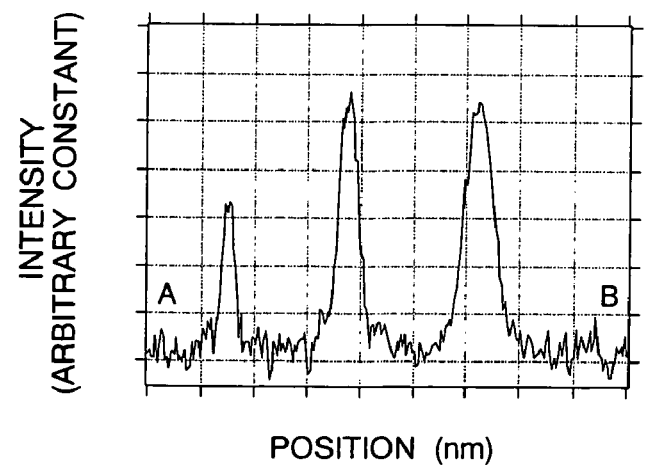
FIG. 7B is a graph showing an intensity profile of the elemental map.

Subsequently, FIG. 7A shows the elemental map of Cr which has been obtained under the above conditions by means of the electron spectroscopy. In FIG. 7A, white portions are places where Cr exists. FIG. 7B shows the intensity profile that is obtained from a white line portion shown in FIG. 7A which is the elemental map of Cr. It is understood from the profile that the positions at which Cr exists are expressly shown.

FIGS. 8A to 8C show an example of a case in which the transmission electron microscope image and the elemental map of chrome are displayed in the image display 15, and one portion is measured in length. FIG. 8A shows the transmission electron microscope, and FIG. 8B shows the elemental map of Cr. The layers of Cr are measured by the measurement position designation mark within the elemental map of Cr.

In this example, the film thickness that is obtained by the set magnification of the transmission electron microscope is displayed as a pre-correction of the measurement result of FIG. 8C as in the conventional art. The measurement result is 1.4 nm. However, when the above-mentioned measurement correction is conducted, the film thickness is displayed as a post-correction of the measurement result of FIG. 8C. The measurement result is 1.1 nm. It is understood that the same results as the x-ray reflectivity are obtained from the micro region. The measurement mark is corrected in the elemental map of Cr and different in length from the measurement mark of the transmission electron microscope image.

Figure 9:
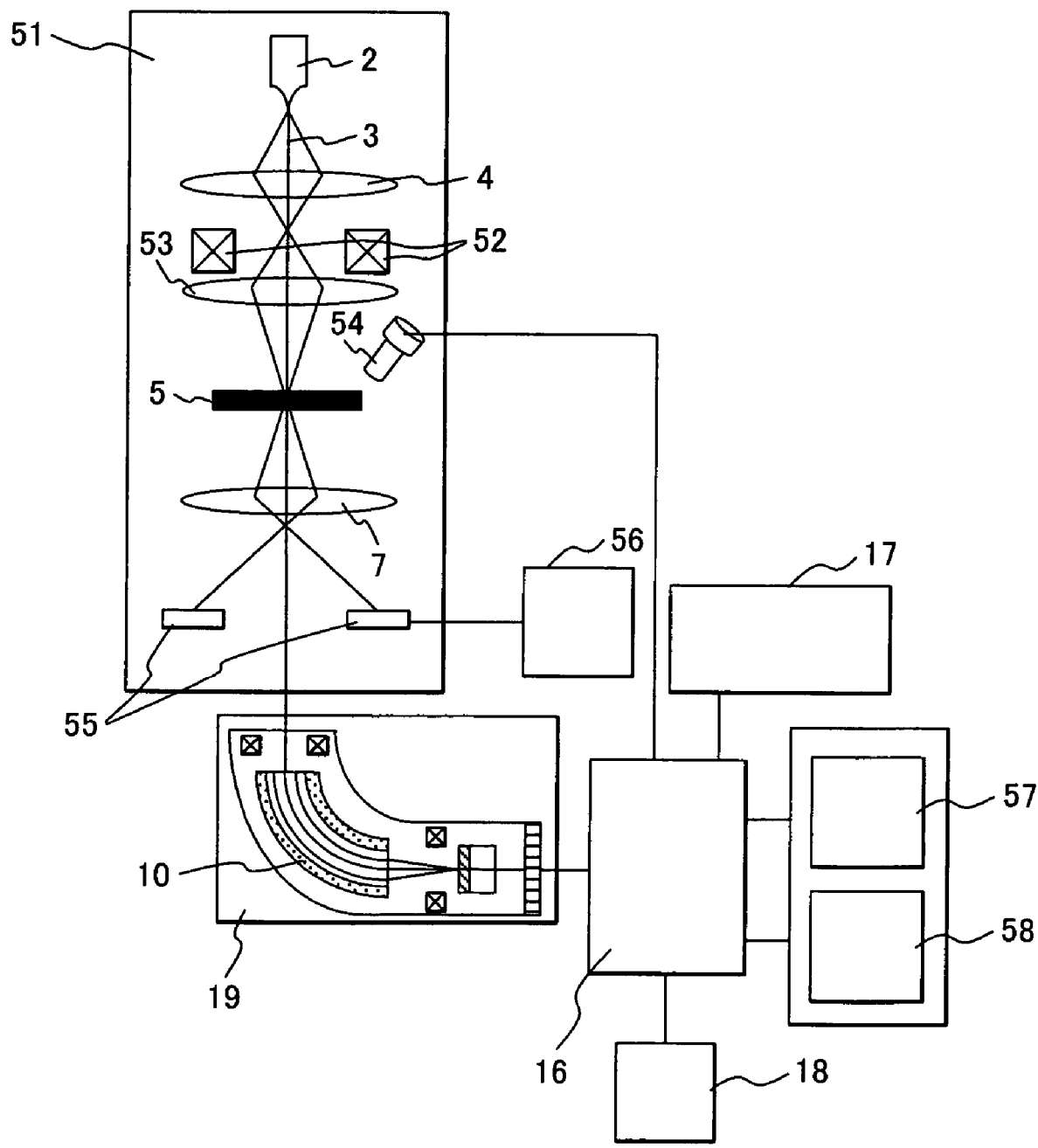
FIG. 9 is a schematic structural diagram showing a thin film evaluating apparatus using a scanning transmission electron microscope with an energy x-ray dispersive spectroscopy and an electron spectroscopy according to the present invention.

FIG. 9 shows a schematic view showing a thin film evaluating device that is equipped with a scanning transmission electron microscope and an energy dispersive x-ray spectroscopy. For simplifying, in FIG. 9, the same functional parts as those in FIG. 1 are denoted by identical symbols in FIG. 1, and their description will be omitted.

In the case of a scanning transmission electron microscope 51, the electron beam 3 that has been emitted from the electron source 2 scans the electron irradiated locations of the specimen 5 with a scanning coil 52. Also, the electron beam 3 is condensed by an objective lens 53, and irradiated onto the specimen 5. The electron beam 3 transmitted by the specimen 5 is detected by a scattered electron detector 55 in each of the electron irradiated locations, and a z-contrast image is displayed in a z-contrast display device 56. Also, an analyzer with which the scanning transmission electron microscope 51 is equipped is formed of an energy x-ray spectroscopy 54 or an electron spectroscopy 19, and the elemental map acquired by such a spectroscopy is displayed in an energy x-ray spectroscopy image display 57 or an electron spectroscopy image display 58.

In the case of measuring the length by using the elemental map that is obtained by the analyzer 19 or 54 with which the scanning transmission electron microscope 51 is equipped, the measurement can be conducted in detail by correcting the measurement with the use of a correction expression other than the above-mentioned correction expression for this apparatus. Also, the film thickness can be measured with respect to a thin film structure having no micro region or crystal structure. In addition, analysis is facilitated because the film thickness can be accurately measured when the defect of a device such as a semiconductor device or a magnetic head device is analyzed.

What is claimed is:

1. A method for evaluating a sample, comprising:
   inputting measurement conditions;
   generating electron beams from an electron source to condense the electron beams to a specimen with a condenser lens;
   enlarging the electron beams transmitted by the specimen with an imaging lens to image an enlarged image of the specimen;
   acquiring an elemental map of the specimen with an element analyzer to display the acquired elemental map; and
   measuring a length of an element on the acquired elemental map of the sample using a predetermined correction coefficient inherent to the element on the acquired elemental map.

2. The method for evaluating a sample according to claim 1, wherein the elemental map is acquired by one of an electron energy loss spectroscopy, an energy dispersive X-ray spectroscopy, and a cathode luminescence.

3. The method for evaluating a sample according to claim 1, comprising displaying a measurement mark that indicates a given length and a numeric value indicative of a length of the measurement mark on the elemental map.

4. The method for evaluating a sample according to claim 3, wherein the measurement mark are displayed having chosen length and tilt.

5. The method for evaluating a sample according to claim 1, wherein the inputting the measurement conditions comprises inputting observation conditions of the length measurement, and wherein the correcting the measurement length uses the inputted observation conditions and the measured length of the elemental map.

6. The method for evaluating a sample according to claim 2, wherein the elemental map is acquired by an electron energy loss spectroscopy, the step of correcting the measured length $R_T$ to obtain a corrected length R is based on a length measuring error $\Delta R$ so as $R=\sqrt{R_T^2-(\Delta R)^2}$, and $$\Delta R = \sqrt{d_c^2 + d_d^2 + d_s^2 + (Z_z)^2} \quad (Ex\ 1)$$

$$d_c = C_c \times \frac{\Delta E}{E_0} \times \beta$$

$$d_d = 0.61 \times \frac{\lambda}{\beta}$$

$$d_s = 0.5 \times C_s \times \beta^3$$

and wherein $C_c$ is a chromatic aberration coefficient, $C_s$ is a spherical aberration coefficient, $\Delta E$ is an energy select slit width, $E_0$ is the acceleration voltage of the electron beam, $\beta$ is a divergence angle of the electron beam, $\lambda$ is a wavelength of the electron beam, and $Z_z$ is the predetermined correction coefficient inherent to the element on the acquired elemental map.

7. The method for evaluating a sample according to claim 1 comprising correcting the measured length by using the measurement conditions based upon predetermined variation in length resulting from the measurement conditions and a predetermined correction coefficient inherent to the element on the acquired elemental map.

8. The method for evaluating a sample according to claim 1 comprising correcting the elemental map using the measurement conditions based upon predetermined variation in length resulting from the measurement conditions and a predetermined correction coefficient inherent to the element on the acquired elemental map, and obtaining a corrected length of an element from the corrected elemental map.

9. An apparatus for evaluating a sample, comprising:
an electron source that generates electron beams;
a condenser lens that condenses the electron beams generated from the electron source to the specimen;
a plurality of imaging lenses including an objective lens that enlarges electron beams transmitted by the specimen and images an enlarged image of the specimen;
an analyzer arranged to acquire an elemental map;
an image display that displays the elemental map taken by the analyzer;
a measurement conditions input device that inputs the measurement conditions;
length measuring means for measuring lengths of an element on the acquired elemental map based on a predetermined correction coefficient inherent to the element on the acquired elemental map.

10. The apparatus for evaluating a sample according to claim 9, wherein the elemental map is acquired by one of an electron energy loss spectroscopy, an energy dispersive X-ray spectroscopy, and a cathode luminescence.

11. The apparatus for evaluating a sample according to claim 9, wherein a distance between two arbitrary points in the elemental map can be measured.

12. the apparatus for evaluating a sample according to claim 9, wherein the image display displays a measurement mark that indicates a given length and a numeric value indicative of a length of the measurement mark.

13. The apparatus for evaluating a sample according to claim 12, wherein the length and tilt of the measurement mark displayed on the image display can be arbitrarily set.

14. The apparatus for evaluating a sample according to claim 9, wherein the measurement conditions input device inputs corrected measurement conditions to correct measurement results based upon the length measurement of the elemental map.

15. The apparatus for evaluating a sample according to claim 14, wherein the measurement conditions input device inputs an observation conditions of a length measurement to correct measurement results based on the length measurement of the elemental map, and the length measuring correcting device corrects the length measurement means according to the measurement conditions and the observation conditions.

16. The apparatus for evaluating a sample according to claim 12, wherein the measurement conditions input device inputs corrected measurement conditions to correct measurement results based upon the length measurement of the elemental map.

17. An apparatus for evaluating a sample, comprising:
an electron source that generates electron beams;
a condenser lens that condenses the electron beams generated from the electron source to the specimen;
a plurality of imaging lenses including an objective lens that enlarges electron beams transmitted by the specimen and images an enlarged image of the specimen;
an analyzer arranged to acquire an elemental map;
a length measuring means for measuring lengths on the elemental map;
a correcting means for correcting measured lengths on the elemental map based upon predetermined variation in length resulting from the measurement conditions used for the acquisition of the elemental map and a predetermined correction coefficient inherent to the element on the acquired elemental map; and
an image display that displays the elemental map taken by the analyzer;
wherein the image display is arranged to display the enlarged image of the specimen and the elemental map taken at the same magnification; and
wherein the image displays is arranged to display one of (a) measurement marks of the enlarged image and the elemental map having substantially equal lengths and different display values indicative of the corrected lengths, and (b) measurement marks of the enlarged image and the elemental map having identical display values indicative of corrected lengths of the measurement mark and different displayed lengths of the measurement marks.

18. The apparatus for evaluating a sample according to claim 16, wherein the measurement conditions input device inputs an observation conditions of a length measurement to correct measurement results based on the length measurement of the elemental map, and the length measuring correcting device corrects the length measurement means according to the measurement conditions and the observation conditions.

* * * * *